(12) United States Patent
Preschel et al.

(10) Patent No.: US 8,895,754 B2
(45) Date of Patent: *Nov. 25, 2014

(54) PROCESS TO MAKE UV RADIATION ABSORBING 2-PHENYL-1,2,3,-BENZOTRIAZOLES

(75) Inventors: Michael Preschel, Hohentengen (DE); Michael Roeder, Gomaringen (DE); Alexander Schlifke-Poschalko, Birsfelden (CH); Kesheng Zhang, Lenzburg (CH)

(73) Assignee: DSM IP Assets B.V., Heerlen (NL)

( * ) Notice: Subject to any disclaimer, the term of this patent is extended or adjusted under 35 U.S.C. 154(b) by 26 days.

This patent is subject to a terminal disclaimer.

(21) Appl. No.: 13/521,761

(22) PCT Filed: Jan. 13, 2011

(86) PCT No.: PCT/EP2011/050395
§ 371 (c)(1),
(2), (4) Date: Jul. 12, 2012

(87) PCT Pub. No.: WO2011/086127
PCT Pub. Date: Jul. 21, 2011

(65) Prior Publication Data
US 2012/0302760 A1  Nov. 29, 2012

(30) Foreign Application Priority Data
Jan. 15, 2010 (EP) .................... 10150832

(51) Int. Cl.
C07D 249/20 (2006.01)
A61K 8/35 (2006.01)
A61Q 17/04 (2006.01)
A61K 8/40 (2006.01)
A61K 8/49 (2006.01)

(52) U.S. Cl.
CPC . *A61K 8/496* (2013.01); *A61K 8/35* (2013.01); *C07D 249/20* (2013.01); *A61Q 17/04* (2013.01); *A61K 8/40* (2013.01)
USPC .......................................... 548/260; 548/261

(58) Field of Classification Search
None
See application file for complete search history.

(56) References Cited

U.S. PATENT DOCUMENTS
2001/0007886 A1   7/2001  Ravichandran et al.

FOREIGN PATENT DOCUMENTS
CN    1 727 338         2/2006
JP    8-208628          8/1996
WO    WO 2010/053917    5/2010

OTHER PUBLICATIONS

International Search Report for PCT/NL2011/050395, mailed Feb. 15, 2011.
Written Opinion of the International Searching Authority for PCT/NL2011/050395, mailed Feb. 15, 2011, (10 pages).
CN 1 727 338, (Feb. 1, 2006) & Deng et al., "Compounds Benzotriazole Category Possess Alkenyl Ester Type Structure Preparation Method", WPI/Thomson, XP007911427.

*Primary Examiner* — Alicia L Otton
(74) *Attorney, Agent, or Firm* — Nixon & Vanderhye P.C.

(57) ABSTRACT

The invention relates to an improved process for the manufacture of novel benzotriazoles as well to novel benzotriazoles obtained by the novel process. This novel economical process provides products in high purity and yields.

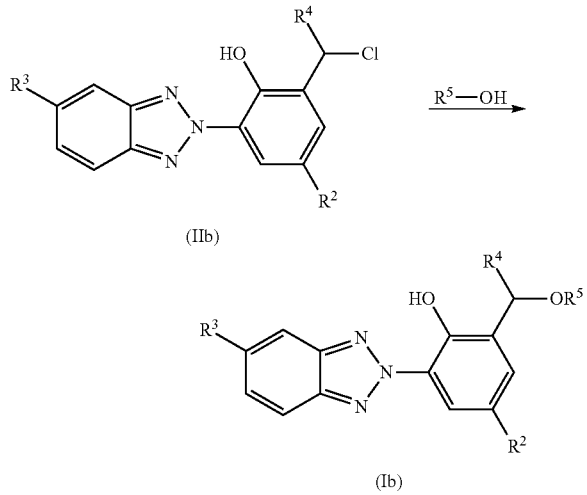

18 Claims, No Drawings

PROCESS TO MAKE UV RADIATION ABSORBING 2-PHENYL-1,2,3,-BENZOTRIAZOLES

This application is the U.S. national phase of International Application No. PCT/EP2011/050395, filed 13 Jan. 2011, which designated the U.S. and claims priority to EP Application No. 10150832.3, filed 15 Jan. 2010.

The invention relates to a process for the manufacture of novel benzotriazoles as well to novel benzotriazoles obtained by the novel process. This novel economical process provides products in high purity and yields.

Sun care products have evolved considerably over the years. Earlier formulations were intended to protect the user from UV-B radiation (UVB) as was once thought that UV-B rays were the most important contributors to wrinkling, skin disease, and skin cancer. However, more recent studies have shown that UV-A radiation (UVA) is equally or even more important in the development of solar damage and skin diseases, such as lupus erythematosus and melanoma and non-melanoma skin cancers. Thus, today's focus is toward eliminating as much of UVA (320-400 nm) and/or UVB (280-320 nm) light as possible. This is reflected by novel regulations e.g. the EU recommendation 2006 which require the UVA protection to be at least one third of the UVB protection provided by the sun-care product or the FDA monograph proposal 2007 which introduces a star rating for UVA protection.

Due to the increasing demand for high SPF sun care products with a UVA protection complying with the above mentioned regulations, more UV-filter substances at elevated levels have to be incorporated into the sun care products;

In order to achieve the UVA protection required by the novel regulations today's sun-care products often contain Butyl Methoxydibenzoylmethane (BMDBM), the only globally approved UVA screening agent.

BMDBM, however, exhibits only a limited solubility in the conventional cosmetic oils used for the solubilisation of solid UV-filter substances in order to enable their incorporation into cosmetic preparations (such as e.g. the cosmetic oils $C_{12-15}$ alkyl benzoate or diisopropyl sebaceate), which is typically less than 20%. As a consequence sun-care products containing high amounts BMDBM require high amounts of such cosmetic oils in order to solubilize BMDBM and avoid a re-crystallization in the product, which in turn, however, often results in an unpleasant oily gritty and/or tacky skin feel of the final products and a reduction in UV protection performance.

Furthermore, BMDBM is photoinstable i.e. it is degraded relatively quickly under the action of sunlight and, as a result, loses its protective action.

Thus, there is an ongoing need for compounds which are able to efficiently stabilize BMDBM and furthermore act as solubilizer for BMDBM in order to reduce the total amount of cosmetic oils used in sun care products. Furthermore, such compounds should be well soluble itself in such cosmetic oils or even be liquid and be accessible via a simple, economically attractive and environmentally benign method in order to be competitive in the market.

It has now surprisingly be found that novel benzotriazoles which are able to efficiently stabilize BMDBM are obtainable in simple, economically attractive and environmentally benign manner by reaction of a (2H-benzotriazol-2-yl)-6-chloromethyl-phenol derivative with an alcohol in the presence of an alkali metal and/or alkaline earth metal carbonate or bicarbonate base to form the respective ether as exemplified below:

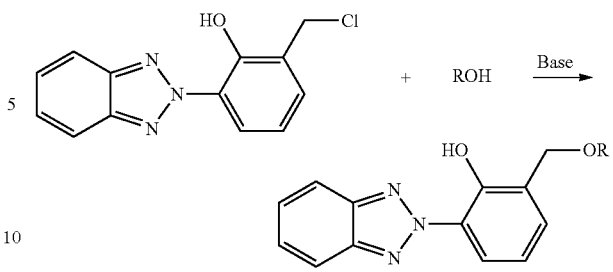

The inventive process results in less coloured reaction mixtures which makes additional purification steps dispensable. Furthermore, the products are obtained in high yields.

Thus, the invention relates to a process for the preparation of benzotriazole derivatives of formula (Ia)

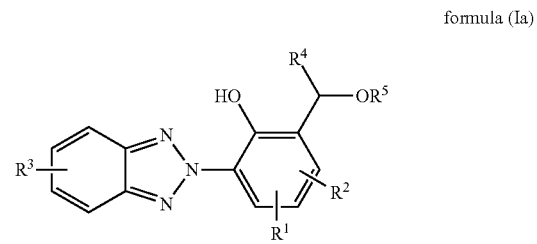

formula (Ia)

wherein
$R^1$ is hydrogen; $C_{1-30}$alkyl; $C_{1-5}$alkoxy; $C_{1-5}$alkoxycarbonyl; $C_{5-7}$cycloalkyl; $C_{6-10}$aryl or aralkyl;
$R^2$ is hydrogen; $C_{1-30}$alkyl; $C_{1-5}$alkoxy; $C_{1-5}$alkoxycarbonyl; $C_{5-7}$cycloalkyl; $C_{6-10}$aryl or aralkyl;
$R^3$ is hydrogen; $C_{1-5}$alkyl; $C_{1-5}$alkoxy or halogen, preferably hydrogen, Cl or hydroxy;
$R^4$ is hydrogen or $C_{1-5}$alkyl;
$R^5$ is $C_{1-30}$alkyl or $C_{5-10}$cycloalkyl.
said process comprising the step of reacting a 2-(2H-benzotriazol-2-yl)-6-chloromethyl-phenol derivative (IIa) with an alcohol $R^5$—OH in the presence of an alkali metal and/or alkaline earth metal carbonate or bicarbonate

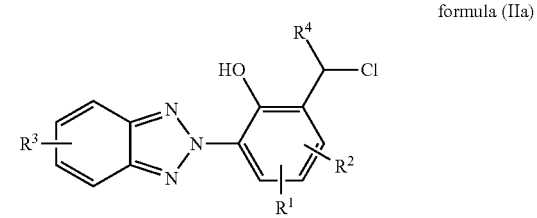

formula (IIa)

In another aspect, the invention relates to a process for the preparation of benzotriazole derivatives of formula (Ib)

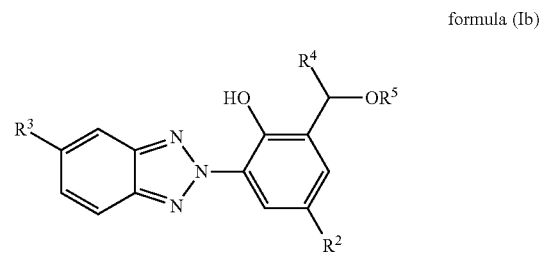

formula (Ib)

wherein
R² is hydrogen; $C_{1-30}$alkyl; $C_{1-5}$alkoxy; $C_{1-5}$alkoxycarbonyl; $C_{5-7}$cycloalkyl; $C_{6-10}$aryl or aralkyl;
R³ is hydrogen; $C_{1-5}$alkyl; $C_{1-5}$alkoxy or halogen, preferably hydrogen or Cl, most preferably hydrogen;
R⁴ is hydrogen or $C_{1-5}$alkyl; and
R⁵ is $C_{1-30}$alkyl or $C_{5-10}$cycloalkyl,
said process comprising the step of reacting a 2-(2H-benzotriazol-2-yl)-6-chloromethyl-phenol derivative (IIb) with an alcohol R⁵—OH in the presence of alkali metal and/or alkaline earth metal carbonate or bicarbonate

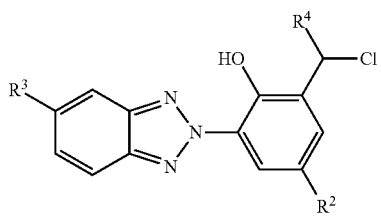

formula (IIb)

In a particular embodiment the invention relates to for the preparation of benzotriazole derivatives of formula (Ic)

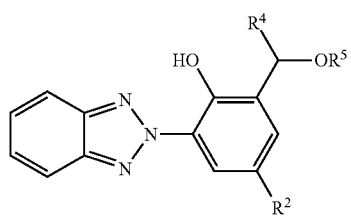

formula (Ic)

wherein
R₂ is hydrogen or $C_{1-12}$alkyl, preferably $C_{1-4}$alkyl, most preferably methyl;
R₄ is hydrogen or $C_{1-2}$alkyl; preferably hydrogen and
R₅ is $C_{1-12}$alkyl or $C_{5-7}$cycloalkyl, preferably $C_{5-10}$alkyl or $C_6$cycloalkyl such as most preferably $C_{6-10}$alkyl or $C_6$cycloalkyl,
said process comprising the step of reacting a 2-(2H-benzotriazol-2-yl)-6-chloromethyl-phenol derivative (IIc) with an alcohol R⁵—OH in the presence of alkali metal and/or alkaline earth metal carbonate or bicarbonate

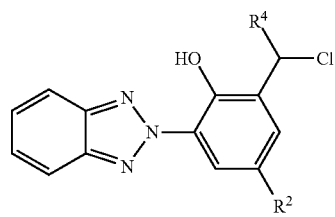

formula (IIc)

In another particular embodiment the invention relates to a process for the preparation of benzotriazol derivatives of formula (Ic) wherein
R₂ is methyl;
R₄ is hydrogen and R₅ is $C_{5-10}$alkyl or $C_6$cycloalkyl such as $C_{6-10}$alkyl or $C_6$cycloalkyl such as in particular 2,5,5-trimethylhexyl, 3,5,5-trimethylhexyl, isoamyl, 2-ethylhexyl or 3,3,5-trimethylcyclohexyl.

The 2-(2H-benzotriazol-2-yl)-6-chloromethyl-phenol derivatives according to the invention can be prepared by known methods in the art and as illustrated in the examples such as e.g. by chloroalkylation of a benzotriazole with an aldehyde R⁴CHO as exemplified below

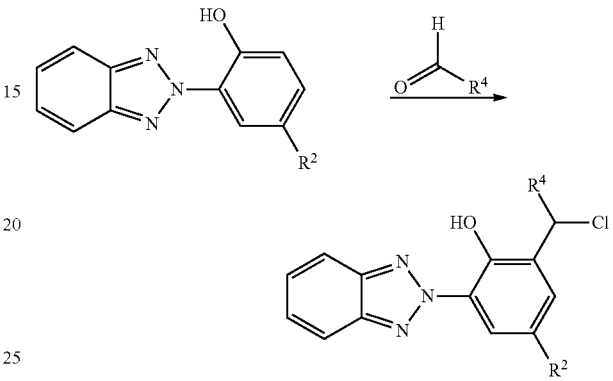

Suitable aldehydes R⁴CHO are in particular formaldehyde and acetaldehyde and sources of formaldehyde such as paraformaldehyde or hexamethylenetetramine.

Particular suitable benzotriazoles for the chloralkylation are 2-(2H-benzotriazol-2-yl)-4-methylphenol [CAS 2440-22-4], 2-(2H-benzotriazol-2-yl)-4-(1,1,3,3-tetramethyl-butyl)phenol [CAS 3147-75-9], and 2-(2H-benzotriazol-2-yl)-4-tert-butyl-phenol [CAS 3846-71-7].

The chloroalkylation can be performed according to known methods for reacting aromatic compounds with hydrogen chloride and an appropriate aldehyde in the presence of a Lewis acid or a proton acid as a catalyst or mixtures thereof. The amount of aldehyde employed in the chloroalkylation reaction may be the stoichiometric amount, i.e., the amount which provides one R⁴ group per benzotriazole. Preferably a slight excess is used in order to achieve full conversion and good yields. Particularly, zinc chloride is used as catalyst and the reaction is carried out in acetic acid. The reaction temperature may vary from about 70° C. to 130° C. Preferably, the reaction temperature ranges from about 70° C. to 100° C., even more preferably from about 65-85° C. The amount of hydrogen chloride used in the reaction is usually at least about one mol equivalent, based on the amount of the benzotriazole; and it is generally introduced by bubbling it through the reaction mixture or by pressurizing the reaction vessel with it.

If the benzotriazole derivatives (Ia-c) according to the invention exhibit one or more stereocenter the present invention encompasses the optically pure isomers or pure enantiomers as well as mixtures of different isomers, e.g. racemates, and/or mixtures of rotamers. If applicable, mixtures of different isomers, e.g. racemates, and/or mixtures of rotamers are preferred.

The term $C_{1-30}$alkyl (encompassing $C_{1-2}$alkyl, $C_{1-5}$alkyl, $C_{5-10}$alkyl, $C_{6-10}$alkyl, $C_{1-12}$alkyl) denotes to straight-chain or branched alkyl radicals like methyl, ethyl, n-propyl, isopropyl, n-butyl, sec.butyl, tert.butyl, amyl, isoamyl or ter.t.amyl, hexyl, 2-ethylhexyl, heptyl, octyl, isooctyl, nonyl, decyl, undecyl, dodecyl, tetradecyl, pentadecyl, hexadecyl, heptadecyl, octadecyl or eicosyl without being limited thereto. Particularly advantageous are branched alkyl radicals such as particularly branched $C_{5-12}$alkyl radicals, more particularly branched $C_{5-10}$alkyl radicals such as branched $C_{6-10}$alkyl radicals such as e.g. 2,5,5-trimethylhexyl, 3,5,5-trimethylhexyl, isoamyl or 2-ethylhexyl as the respective benzotriazoles exhibit a particularly good solubility in the cosmetic oils Myritol 318 [INCI: Capric/Caprylic Triglyceride] respectively Finsolv TN [INCI: $C_{12-15}$ Alkylbenzoate].

Therefore, in a specific embodiment the invention also relates to a process according to the invention, wherein $R^2$ is methyl; $R^4$ is hydrogen and $R^5$ is a branched alkyl radical such as in particular a branched $C_{5-10}$alkyl radical such as most in particular 2,5,5,-trimethylhexyl, 3,5,5-trimethylhexyl, isoamyl, 2-ethylhexyl or 3,3,5-trimethyl-cyclohexyl.

The term cycloalkyl denotes to unsubstituted or $C_{1-10}$alkyl, in particular $C_{1-5}$alkyl substituted cyclic, bicyclic or tricyclic hydrocarbon residues such as in particular cyclopentyl, cyclohexyl, cycloheptyl or decahydronaphtyl. Preferably, the term cycloalkyl denotes to unsubstituted or $C_{1-2}$alkyl substituted cyclopentyl, cyclohexyl or cycloheptyl such as in particular to unsubstituted or methyl substituted cyclohexyl such as most in particular cyclohexyl or 3,3,5-trimethyl-cyclohexyl. Particularly advantageous are methyl substituted cyclohexyl radicals such as particularly 3,3,5-trimethylcyclohexyl.

The term $C_{1-5}$alkoxy refers for example to methoxy, ethoxy, propoxy, butyloxy or pentyloxy.

The term $C_{6-10}$aryl refers for example to naphthyl or phenyl, preferably to phenyl.

Suitable alkali metal and/or alkaline earth metal carbonates or bicarbonates encompass sodium carbonate, potassium carbonate, lithium carbonate, calcium carbonate, magnesium carbonate, sodium hydrogencarbonate, potassium hydrogencarbonate, lithium hydrogencarbonate and magnesium hydrogencarbonate.

The amount of the alkali metal and/or alkaline earth metal carbonates or bicarbonates used in the process according to the invention is generally selected in the range of 0.9 to 1.5 mol-% such as particularly in the range of 1 to 1.1 mol-%, based on the 2-(2H-benzotriazol-2-yl)-6-chloromethyl-phenol derivative.

Advantageously alkali metal carbonates such as in particular sodium carbonate, potassium carbonate or lithium carbonate are used in the process according to the invention. Particular good results are obtained if lithium carbonate is used as base in the processes according to the invention as this, next to a decreased discoloration, furthermore leads to a decreased formation of unwanted side products such as in particular of the respective 2-(2H-Benzotriazol-2-yl)-6-hydroxymethylphenol derivative compared to other alkali metal carbonates.

Suitable alcohols $R^5OH$ according to the present invention are e.g. methanol, ethanol, n-propanol, i-propanol, 1-butanol, 2-butanol, tert.-butanol, 2-ethyl-1-butanol, 2-methyl-1-butanol, 1-pentanol, 2-pentanol, 3-pentanol, 4-methyl-2-pentanol, 3-methyl-1-pentanol, 2-methyl-1-pentanol, 1-hexanol, 2-hexanol, 3-hexanol, 2-methyl-3-hexanol, 5-methyl-2-hexanol, 5-methyl-1-hexanol, 2,2-dimethyl-3-hexanol, 4-ethyl-3-hexanol, 3-methyl-1-hexanol, 2,5-dimethyl-3-hexanol, 1-heptanol, 2-heptanol, 3-heptanol, 5-methyl-3-heptanol, 2,4-dimethyl-3-heptanol, 6-methyl-2-heptanol, 4-methyl-3-heptanol, 2,6-dimethyl-4-heptanol, 2,6-dimethyl-2-heptanol, 1-octanol, 2-octanol, 3-octanol, 4-octanol, 2-butyl-1-octanol, 3,7-dimethyl-1-octanol, 1-nonanol, 2-nonanol, 3-nonanol, 4-nonanol, 5-nonanol, 2,6,8-trimethyl-4-nonanol, 1-decanol, 2-decanol, 4-decanol, 1-undecanol, 2-undecanol, 3-undecanol, 6-undecanol, 1-dodecanol, cyclohexanol, 4-ethylcyclohexanol, 4-methylcyclohexanol, 3-methylcyclohexanol, 2-methylcyclohexanol, 2,3-dimethylcyclohexanol, 4-butylcyclohexanol, 2-tert-butylcyclohexanol, 4-tert-butyl-cyclohexanol, 4-tert-amylcyclohexanol, cyclohexanemethanol, 2-cyclohexylethanol, 3-cyclohexyl-1-propanol, 4-methyl-1-cyclohexanemethanol, 2-cyclohexylcyclohexanol, 1-cyclohexyl-1-butanol, cyclooctanol, cyclopentanol, cycloheptanol, decahydro-2-naphthol, borneol, isoborneol, isopinocampheol, menthol, isomenthol, neomenthol, myrtanol, tetrahydrolavandulol, 2-norboranemethanol, 1-adamantanol, 2-adamantanol, isoamylalcohol such as in particular hexanol, isoamylalcohol, 2,5,5-trimethylhexan-1-ol, 2-ethylhexanol, 3,3,5-trimethylcyclohexanol or 3,5,5-trimethylhexan-1-ol as well as mixtures thereof.

It is particularly advantageous to use branched alkyl alcohols in the processes according to the invention, such as branched $C_{5-12}$ alcohols, in particular branched $C_{5-10}$ alcohols or even branched $C_{6-10}$ alcohols such as e.g. isoamylalcohol, 2,5,5-trimethylhexan-1-ol, 2-ethylhexanol or 3,5,5-trimethylhexan-1-ol as this leads to particularly well suitable benzotriazoles in the cosmetic oils selected from Myritol 318 [INCI Capric/Caprylic Triglyceride] and Finsolv TN [INCI C12-15 Alkylbenzoate]. Further advantageous is the use of methyl substituted cyclohexanols such as e.g. 3,3,5-trimethylcyclohexanol.

The process according to the present invention is typically conducted at 50-100° C. and is completed in about 1-15 hours.

Pressure is not critical to the present process, except to the extent that the selection of a particular pressure may facilitate rapid removal of the water released in the reaction medium.

If the reaction is carried out at normal pressure, the reaction temperature is preferably chosen in the range of about 70 to 90° C.

The reaction can either be carried out in an excess of the corresponding alcohol $R^5$—OH (in the absence of any further solvents) or in the presence of an inert solvent.

If no inert solvent is present in the process according to the invention, then the alcohol $R^5$—OH is preferably used in a large excess. Advantageously the molar ratio of alcohol $R^5$—OH to the 2-(2H-benzotriazol-2-yl)-6-chloromethyl-phenol derivative is at least 5:1. Preferably, in the absence of an inert solvent, the molar ratio of alcohol $R^5$—OH to the respective 2-(2H-benzotriazol-2-yl)-6-chloromethyl-phenol derivative is selected in the range of about 5:1 to 100:1 such as particularly in the range of about 10:1 to 15:1.

The reaction, however, can also be carried out in a wide range of inert solvents such as in particular in acetone, acetonitrile, N,N-dimethylformamide, tetrahydrofuran, dioxane, benzene or toluene. In the presence of an inert solvent, the alcohol $R^5$—OH is preferably used in a small excess. Advantageously the molar ratio of the alcohol $R^5$—OH to the respective 2-(2H-benzotriazol-2-yl)-6-chloromethyl-phenol derivative is selected in the range of at most 5:1 and at least 1:1, such as from about 3:1 to 1:1 and in particular from about 2:1 to 1.1:1.

The presence of an inert solvent is in particular advantageous if the alcohol $R^5$—OH has a high boiling point such as e.g. a boiling point above 100° C. or even above 150° C. (such as e.g. 2-ethylhexanol) since it takes extra work-up efforts and costs to remove high boiling alcohols.

The amount of solvent can easily be adjusted by a person skilled in the art and is e.g. selected in the range of 0.25 to 10 times the amount of $R^5$—OH [g/g] such as e.g. 2 to 10 times the amount of $R^5$—OH [g/g].

A particular suitable inert solvent is toluene as the water released in the reaction medium can be removed by azeotropic co-evaporation.

Catalysis is not generally necessary in the process according to the present invention however, if deemed appropriate, the reaction rate (i.e. time of turnover) can be further improved by the addition of a catalyst such as a soluble iodide salt, a phase transfer catalysts such as tetrabutylammonium phosphate (TBAP), triethylammonium bicarbonate (TEAB) or lithium bromide (LiBr).

If a catalyst is present, the amount of the catalyst is preferably chosen in the range of 5 to 20 mol-% such as in the range of 8 to 15 mol-% based on the respective 2-(2H-benzotriazol-2-yl)-6-chloromethyl-phenol derivative.

If a solvent such as in particular toluene is used in the process according to the invention and the molar excess of the alcohol $R^5$—OH to the respective 2-(2H-benzotriazol-2-yl)-6-chloromethyl-phenol derivative is at most 5:1 and at least 1:1, such as from about 3:1 to 1:1 and in particular from about 2:1 to 1.1:1 based on the amount of the respective 2-(2H-benzotriazol-2-yl)-6-chloromethyl-phenol derivative advantageously a catalyst such as in particular lithium bromide is used as this significantly decreases the reaction times respectively increases the time of turnover.

Particular advantageous results are obtained if the reaction is carried out in toluene, the alkali metal and/or alkaline earth metal carbonate or bicarbonate is lithium carbonate and the catalyst is lithium bromide as this significantly increases the time of turnover. Thus, in a particular embodiment the process according to the present invention is carried out in toluene, the alkali metal and/or alkaline earth metal carbonate or bicarbonate is lithium carbonate, the molar ratio of the alcohol $R^5$—OH to the respective 2-(2H-benzotriazol-2-yl)-6-chloromethyl-phenol derivative is selected in the range of at most 5:1 and at least 1:1, such as from about 3:1 to 1:1 and in particular from about 2:1 to 1.1:1, the catalyst is lithium bromide used in an amount ranging from about 5 to 20 mol-% such as in an amount ranging from about 8 to 15 mol-% based on the respective 2-(2H-benzotriazol-2-yl)-6-chloromethyl-phenol derivative. Even more preferably, the alcohol $R^5$—OH is a branched alkyl alcohol such as most in particular 2-ethylhexanol and the 2-(2H-benzotriazol-2-yl)-6-chloromethyl-phenol derivative is 2-(2H-benzotriazol-2-yl)-6-chloromethyl-4-methylphenol.

In another embodiment of the invention, the invention relates to benzotriazole derivatives obtained according to a process of the present invention.

The process according to the invention can in principle be carried out in any reactor suitable for the respective reaction type. Without restricting generality, the following are mentioned by way of example: suspension reactor, stirred tank, stirred tank cascade, tubular reactor, shell-type reactor, shell and tube reactor, fixed-bed reactor, fluidized-bed reactor, reactive distillation column.

The following examples are provided to further illustrate the processes of the present invention. These examples are illustrative only and are not intended to limit the scope of the invention in any way.

EXAMPLE 1

Synthesis of 2-(2H-Benzotriazol-2-yl)-6-chloromethyl-4-methyl-phenol

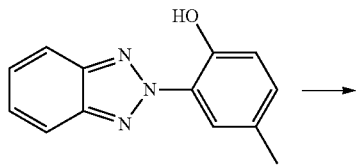

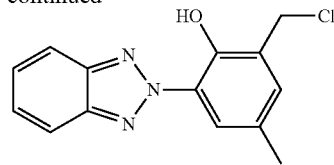

A mixture of 2-(2H-benzotriazol-2-yl)-4-methyl-phenol (100.0 g, 0.44 mol), paraformaldehyde (26.4 g, 0.88 mol), sulphuric acid (10.9 g, 110 mmol), conc. HCl (200 mL), and acetic acid (500 mL) is heated to 90° C. for six hours. The precipitated product is isolated by filtration and washed subsequently with AcOH, AcOH:heptane (1:1), and heptane and dried at 45° C. (95% yield).

EXAMPLE 2

Comparison of Various Bases

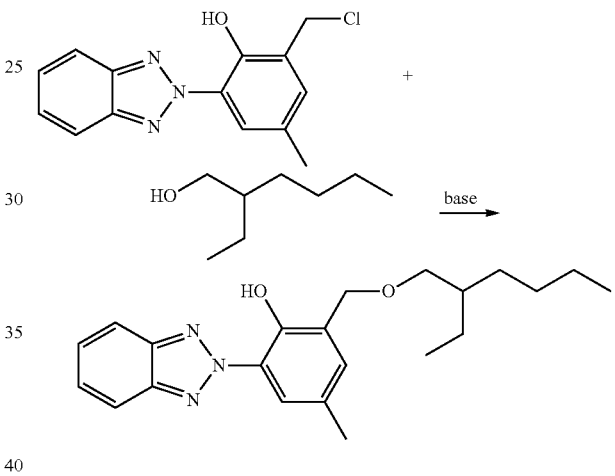

2-(2H-Benzotriazol-2-yl)-6-chloromethyl-4-methylphenol (1.0 g, 3.7 mmol) is suspended in 2-ethylhexan-1-ol (4.0 g, 31 mmol) at 80° C. 1.1 equivalent of the respective base is added and the mixture is stirred for 15 minutes at 80° C. The turnover and impurity profile is determined by means of HPLC analysis. The colour is analysed visually.

In case of sodium methoxide (NaOMe, entry 5) the base is first combined with 2-ethylhexan-1-ol and methanol is removed by distillation under vacuum at 80° C. Subsequently 2-benzotriazol-2-yl-6-chloromethyl-4-methyl-phenol is added and the reaction mixture is stirred 15 minutes at 80° C.

TABLE 1

| entry | base | Turnover* | side products# | Colour |
|---|---|---|---|---|
| 1 | $Na_2CO_3$ | 100% | 4.4% benzylalcohol derivative | slightly yellow |
| 2 | $Li_2CO_3$ | 100% | 0.4% | slightly yellow |
| 3 | $K_2CO_3$ | 100% | 3.0% | slightly yellow |
| 4 | Na | 100% | ~0.5-1% oligomers | orange |
| 5 | NaOMe | 100% | 0.5% benzylalcohol derivative & ~0.5-1% oligomers | orange |
| 6 | NaH | 100% | ~0.5-1% oligomers | orange |
| 7 | tBuOK | 100% | 1.0% | orange |

*i.e. total consumption of 2-(2H-benzotriazol-2-yl)-6-chloromethyl-4-methyl-phenol
i.e. amount of side products detected As can be retrieved from table 1, only the use of alkali metal carbonates leads to slightly colored products whereas the use of other bases such as Na, NaOME, NaH or tBuOK results in a strong discoloration. Furthermore, the use of lithium carbonate further reduces the formation of side products.

EXAMPLE 3

Comparison of Sodium Carbonate and Lithium Carbonate in an Inert Solvent

A suspension of 2-(2H-benzotriazol-2-yl)-6-chloromethyl-4-methyl-phenol (50.0 g, 183 mmol), 2-ethylhexan-1-ol (50.0 g, 384 mmol), lithium bromide (1.6 g, 18 mmol), and 1.1 equivalent of the carbonate in toluene (150.0 g) is stirred under reflux for 3 hours, while generated water is continuously removed by azeotropic distillation. The turnover and impurity profile is determined after 3 hours by means of HPLC analysis. The colour is analysed visually.

TABLE 2

| entry | base | cat. | turnover | side products | colour |
|---|---|---|---|---|---|
| 1 | $Li_2CO_3$ | LiBr | 98.7% | 0.0% | Slightly yellow |
| 2 | $Na_2CO_3$ | LiBr | 44.1% | 8.6% | Slightly yellow |

As can be retrieved from table 2, the time of turnover in an inert solvent, i.e. toluene is significantly increased if lithium carbonate instead of sodium carbonate is used as a base in the presence of a lithium bromide as catalyst. Furthermore, the side product formation is significantly lower.

The lithium carbonate batch has been further worked up by addition of heptane (100 mL) and extraction of the reaction mixture with water (100 mL) at 80° C. The aqueous phase is washed with heptane (50 mL). The combined organic phases are washed with 0.1 M HCl (100 mL), filtered and heptane is removed by evaporation. Residual alcohol is removed at 60° C. under high vacuum and recovered. The resulting product is obtained in 93% yield with an HPLC purity of 98%.

EXAMPLE 4

2-(2H-Benzotriazol-2-yl)-6-(3-methyl-butoxymethyl)-4-methyl-phenol

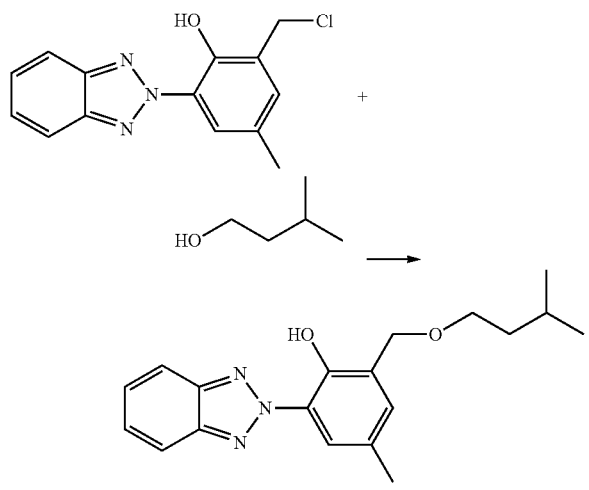

2-(2H-Benzotriazol-2-yl)-6-chloromethyl-4-methyl-phenol (10.0 g, 33 mmol) is suspended in a mixture of isoamyl alcohol (35 g, 0.4 mol) and acetone (5 g) and stirred at 80° C. for 30 minutes. Sodium carbonate (4.7 g, 44 mmol) is added and the slightly yellow reaction mixture is stirred at 80° C. for 30 minutes. Acetone is removed under vacuum, salts are filtered off and the reaction mixture is evaporated to dryness. The residue is dissolved in ethyl acetate and extracted with aqueous citric acid (5%) and brine. The organic layer is dried over sodium sulphate, filtered and evaporated to dryness. The crude product is purified by column chromatography (ethyl acetate/heptane 1:12) to yield 7.0 g of 2-(2H-Benzotriazol-2-yl)-6-(3-methyl-butoxymethyl)-4-methyl-phenol.

EXAMPLE 5

2-(5-Chloro-benzotriazol-2-yl)-6-(2-ethylhexyloxymethyl)-4-methyl-phenol

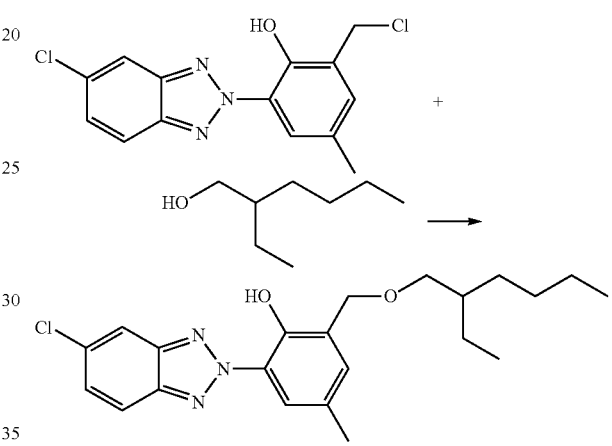

2-(5-Chloro-2H-benzotriazol-2-yl)-6-chloromethyl-4-methyl-phenol (5.0 g, 16 mmol) is suspended in a mixture of 2-ethylhexanol (20.0 g, 154 mmol) and acetone (5 g) and stirred at 80° C. for 15 minutes. Sodium carbonate (3.4 g, 32 mmol) is added. The slightly yellow reaction mixture is stirred at 80° C. for 3 hours and evaporated to dryness. The residue is dissolved in ethyl acetate and extracted with aqueous citric acid (5%) and brine. The organic layer is dried over sodium sulphate, filtered and evaporated to dryness. The crude product is purified by column chromatography (ethyl acetate/heptane 1:12) to yield 4.9 g of 2-(5-Chloro-benzotriazol-2-yl)-6-(2-ethylhexyloxymethyl)-4-methyl-phenol.

EXAMPLE 6

2-(5-Chloro-2H-benzotriazol-2-yl)-4-methyl-6-(3-methyl-butoxymethyl)-phenol

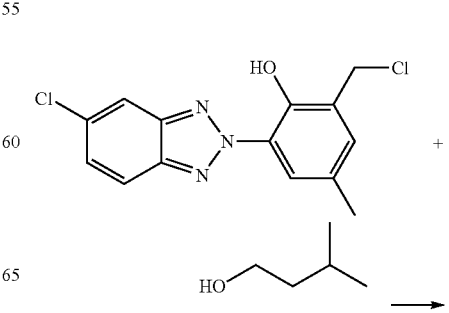

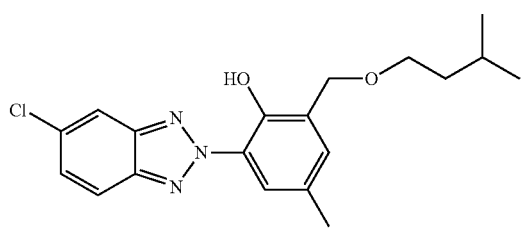

2-(5-Chloro-2H-benzotriazol-2-yl)-6-chloromethyl-4-methyl-phenol (5.0 g, 16 mmol) is suspended in a mixture of isoamyl alcohol (20.0 g, 227 mmol) and acetone (5 g) and stirred at 80° C. for 15 minutes. Sodium carbonate (2.1 g, 20 mmol) is added. The slightly yellow reaction mixture is stirred at 80° C. for 2 hours and evaporated to dryness. The residue is dissolved in ethyl acetate and extracted with aqueous citric acid (5%) and brine. The organic layer is dried over sodium sulphate, filtered and evaporated to dryness. The crude product is purified by column chromatography (ethyl acetate/heptane 1:12) to yield 4.7 g of 2-(5-Chloro-2H-benzotriazol-2-yl)-4-methyl-6-(3-methyl-butoxymethyl)-phenol.

EXAMPLE 7

2-Ethyl-hexanoic Acid 3-(2H-benzotriazol-2-yl)-2-hydroxy-5-methyl-benzyl Ester

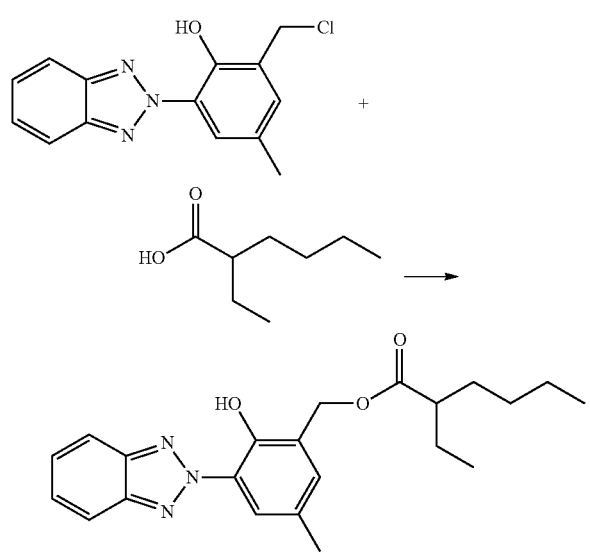

2-(2H-Benzotriazol-2-yl)-6-chloromethyl-4-methyl-phenol (10.0 g, 33 mmol) is suspended in a mixture of 2-ethyl-hexanoic acid (11.9 g, 82 mmol) and tetrahydrofuran (75 g) and stirred at 70° C. for 30 minutes. Sodium carbonate (10.5 g, 99 mmol) is added. The reaction mixture is stirred at 60° C. for 15 minutes and evaporated to dryness. The residue is dissolved in ethyl acetate and extracted with an aqueous potassium carbonate solution (10%) and brine. The organic layer is dried over sodium sulphate, filtered and evaporated to dryness. The crude product is purified by column chromatography (ethyl acetate/heptane 1:12) to yield 11.2 g of 2-Ethyl-hexanoic acid 3-(2H-benzotriazol-2-yl)-2-hydroxy-5-methyl-benzyl ester.

EXAMPLE 8

3-Methyl-butyric Acid 3-(2H-benzotriazol-2-yl)-2-hydroxy-5-methyl-benzyl Ester

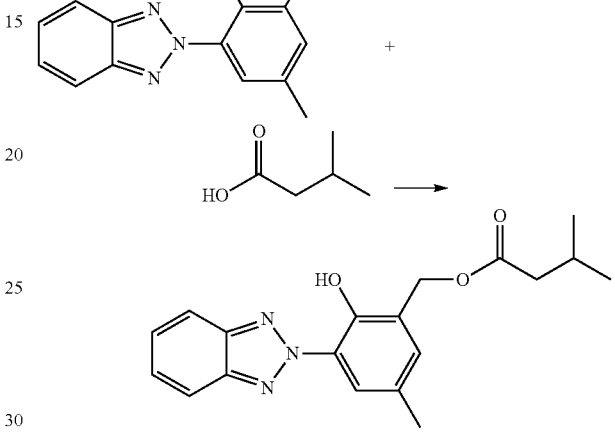

2-(2H-Benzotriazol-2-yl)-6-chloromethyl-4-methyl-phenol (10.0 g, 33 mmol) is suspended in a mixture of 2-isovaleric acid (8.4 g, 82 mmol) and tetrahydrofuran (75 g) and stirred at 70° C. for 30 minutes. Sodium carbonate (10.5 g, 99 mmol) is added. The reaction mixture is stirred at 60° C. for 15 minutes and evaporated to dryness. The residue is dissolved in ethyl acetate and extracted with an aqueous potassium carbonate solution (10%) and brine. The organic layer is dried over sodium sulphate, filtered and evaporated to dryness. The crude product is purified by column chromatography (ethyl acetate/heptane 1:12) to yield 11.5 g of 3-Methyl-butyric acid 3-(2H-benzotriazol-2-yl)-2-hydroxy-5-methyl-benzyl ester.

EXAMPLE 9

3,3'-Bis(2H-benzotriazol-2-yl)-2,2'-dihydroxy-5,5'-dimethylbenzyl Ether

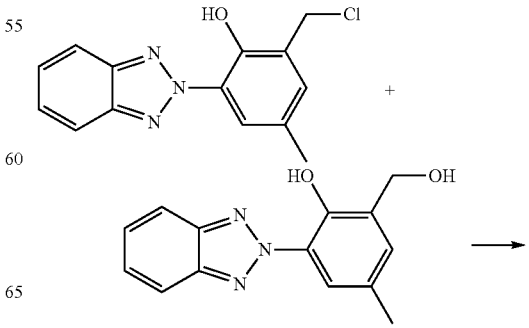

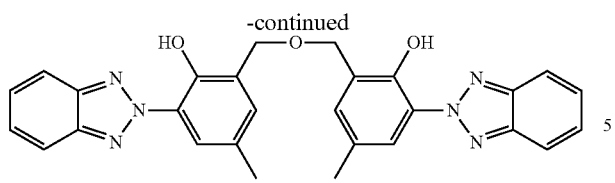

To a suspension of 2-(2H-Benzotriazol-2-yl)-6-chloromethyl-4-methyl-phenol (1.1 g, 3.9 mmol) and 2-(2H-benzotriazol-2-yl)-6-hydroxymethyl-4-methyl-phenol (1.1 g, 3.9 mmol) in toluene (50 mL) sodium carbonate (456 mg, 4.3 mmol) is added. The reaction mixture is stirred at 100° C. for 4 hours. The precipitated product is filtered off, washed with water and tetrahydrofuran, and dried at 70° C. under vacuum to yield 1.3 g of 3,3'-Bis(2H-benzotriazol-2-yl)-2,2'-dihydroxy-5,5'-dimethylbenzyl ether.

EXAMPLE 10

Determination of the Solubility in Cosmetic Solvents 1.5 g of a cosmetic solvent (Capric/Caprylic Triglyceride (Mygliol 318) and $C_{12-15}$ Alkylbenzoate (Finsolv TN)) is saturated with the respective Benzotriazol-derivative by adding 0.2 g portions while stirring at room temperature. The saturated solution is stirred for 7 days at room temperature. 1 ml of the supernatant is centrifuged and filtered in order to obtain a clear solution. The concentration of the Benzotriazol-derivative is determined by means of HPLC.

TABLE 3

| Compound of example | Benzotriazole of formula (Ib) wherein | | Derivative | solubility | |
|---|---|---|---|---|---|
| | $R^3$ | $R^5$ | | Myritol 318 | Finsolv TN |
| 3 | H | —$CH_2CH(C_2H_5)C_4H_9$ (2-Ethylhexyl) | Ether | 66% | 64% |
| 7 | H | —$COCH_2CH(C_2H_5)C_4H_9$ (2-Ethylhexylcarbonyl) | Ester | 24% | 42% |
| 4 | H | —$C_2H_4CH(CH_3)_2$ (Isoamyl) | Ether | 36% | 37% |
| 8 | H | —$COC_2H_4CH(CH_3)_2$ (Isoamylcarbonyl) | Ester | 6% | 8% |
| 6 | Cl | —$C_2H_4CH(CH_3)_2$ (Isoamyl) | Ether | 12% | 19% |
| 9 | H | 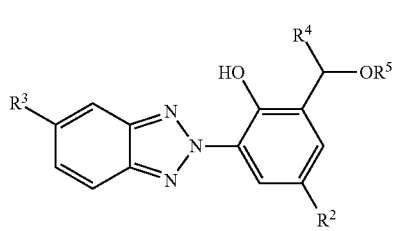 | Bis-Ether | 0.01% | 0.02% |

As can be retrieved from table 3 the alkyl-ether derivatives show a significantly higher solubility compared to the corresponding ester derivatives or the bis-ether of example 9.

The invention claimed is:

1. A process for the manufacture of benzotriazole derivatives of formula (Ib):

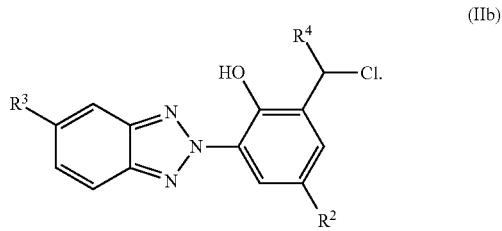

said process comprising the step of reacting a 2-(2H-benzotriazol-2-yl)-6-chloromethyl-phenol derivative of formula (IIb):

(IIb)

with an alcohol of the formula $R^5$—OH in the presence of a base which is at least one selected from the group consisting of an alkali metal carbonate, an alkaline earth metal carbonate, an alkali metal bicarbonate and an alkaline earth metal bicarbonate, wherein in the formulas:
$R^2$ is hydrogen; $C_{1-30}$ alkyl; $C_{1-5}$ alkoxy; $C_{1-5}$ alkoxycarbonyl; $C_{5-7}$ cycloalkyl; $C_{6-10}$ aryl or aralkyl;
$R^3$ is hydrogen; $C_{1-5}$alkyl; $C_{1-5}$alkoxy or halogen;
$R^4$ is hydrogen or $C_{1-5}$alkyl; and
$R^5$ is $C_{1-30}$alkyl or $C_{5-10}$cycloalkyl.

2. The process according to claim 1 wherein $R^2$ is hydrogen or $C_{1-12}$ alkyl, $R^3$ is hydrogen; $R^4$ is hydrogen or $C_{1-2}$ alkyl; and $R^5$ is $C_{1-12}$ alkyl or $C_{5-7}$ cycloalkyl.

3. The process according to claim 2, wherein $R^2$ is $C_{1-4}$ alkyl, $R^4$ is hydrogen and $R^5$ is $C_{5-10}$ alkyl or $C_6$ cycloalkyl.

4. The process according to claim 1, wherein $R^5$ is a branched $C_{1-30}$ alkyl or a methyl substituted cyclohexyl radical.

5. The process according to claim 1, wherein $R^2$ is methyl, $R^3$ and $R^4$ are hydrogen and $R^5$ is 2,5,5,-trimethylhexyl, 3,5,5-trimethylhexyl, isoamyl, 2-ethylhexyl or 3,3,5-trimethylcyclohexyl.

6. The process according to claim 1, wherein the base is used in an amount of 0.9 to 1.5 mol-% based on the 2-(2H-benzotriazol-2-yl)-6-chloromethyl-phenol derivative.

7. The process according to claim 6, wherein the base is used in an amount of 1 to 1.1 mol-% based on the 2-(2H-benzotriazol-2-yl)-6-chloromethyl-phenol derivative.

8. The process according to claim 1, wherein the base is an alkali metal carbonate.

9. The process according to claim 8, wherein the base is lithium carbonate.

10. The process according to claim 1, wherein the process is conducted at a reaction temperature in a range of 70 to 90° C.

11. The process according to claim 1, wherein the reaction is carried out in the absence of an inert solvent and the molar ratio of the alcohol of the formula $R^5$—OH to the 2-(2H-benzotriazol-2-yl)-6-chloromethyl-phenol derivative is at least 5:1.

12. The process according to claim 1, wherein the reaction is carried out in the presence of an inert solvent.

13. The process according to claim 12, wherein the inert solvent is toluene.

14. The process according to claim 12, wherein the molar ratio of the alcohol $R^5$—OH to the 2-(2H-benzotriazol-2-yl)-6-chloromethyl-phenol derivative is in a range of 5:1 to 1:1.

15. The process according to claim 12, wherein the reaction is conducted in the presence of lithium bromide.

16. The process according to claim 15, wherein the lithium bromide is present in an amount of 5 to 20 mol-% based on the 2-(2H-benzotriazol-2-yl)-6-chloromethyl-phenol derivative.

17. The process according to claim 16, wherein the lithium bromide is present in an amount of 8 to 15 mol-% based on the 2-(2H-benzotriazol-2-yl)-6-chloromethyl-phenol derivative.

18. The process according to claim 1, wherein $R^3$ is hydrogen or chlorine.

\* \* \* \* \*